United States Patent [19]

Papay

[11] 4,375,766

[45] Mar. 8, 1983

[54] DEVICE FOR TESTING RIMS OF WHEELS

[75] Inventor: Roger Papay, Bourg-la-Reine, France

[73] Assignee: Messier-Hispano-Bugatti, Montrouge, France

[21] Appl. No.: 204,593

[22] Filed: Nov. 6, 1980

[30] Foreign Application Priority Data

Dec. 19, 1979 [FR] France .................. 79 31093

[51] Int. Cl.³ .................. G01N 3/36; G01M 17/00
[52] U.S. Cl. .................. 73/809; 73/146
[58] Field of Search .................. 73/808–811, 73/146, 577, 583, 593, 118, 662, 663, 806

[56] References Cited

U.S. PATENT DOCUMENTS

| 3,015,949 | 1/1962 | Arnold | 73/662 |
| 3,559,468 | 2/1971 | Jansen et al. | 73/808 |
| 3,961,525 | 6/1976 | Himmler | 73/808 |

FOREIGN PATENT DOCUMENTS

| 2827728 | 1/1980 | Fed. Rep. of Germany | 73/808 |
| 2854803 | 1/1980 | Fed. Rep. of Germany | 73/810 |

*Primary Examiner*—James J. Gill
*Attorney, Agent, or Firm*—McAulay, Fields, Fisher, Goldstein & Nissen

[57] ABSTRACT

The invention relates to a device for testing vehicle wheel rims. The device comprises means of positioning and holding the rim, means for applying loads on the rim, and is characterized by the fact that the said means for applying loads on the rim comprise, on the one hand, a set of controllable jacks whose heads are able to cooperate with the rim, and on the other hand, a control member to actuate the jacks successively according to a predetermined cycle. The device is particularly useful for testing the rims of aircraft wheels.

17 Claims, 4 Drawing Figures

DEVICE FOR TESTING RIMS OF WHEELS

The present invention relates to a test device for vehicle wheel rims, in particular for aircraft.

Test devices are known, in which a large-diameter fly wheel is driven in rotation by its hub with the aid of an electric motor, and against which a vehicle wheel is applied, for example, one equipped with its pneumatic tire, on which are exerted radial and lateral forces relative to the central axis of the fly wheel. Stress gauges are distributed over the wheel, and when the latter is applied on the fly wheel, driven in rotation, the stresses which the wheel undergoes are given by the gauges which transmit them to the control devices disposed on a panel where the results are analyzed.

This device has drawbacks, one of the most important of which is the time for embodiment of the complete tests of one type of wheel; in the event, for example, that an aircraft wheel is to receive about 10,000 km of tests, at least 20 weeks, in the best of cases, is required to carry out these tests, the velocity of rotation of the fly wheel varying only from 3 to 10 kmh. To this is added tire wear, hence a change of the latter about 25 times, and consequently a substantial loss of time in replacing them (more than 200 hours for about 25 tires), owing to the phenomena of friction and heating of the rubber and plys of the tire. Moreover, another drawback, and a substantial one, of this type of device, is its volume itself; as a matter of fact, the fly wheel measures several meters in diameter, which, obviously, requires an installation to match; and likewise, to drive this fly wheel, an electric motor of considerable power is needed.

By means of the present invention, it is proposed to remedy these various drawbacks by creating, for the purpose, a test device for vehicle wheel rims which simultaneously will be very small in volume compared to the known devices, which will not consume tires, and with which the testing time will be considerably reduced.

More precisely, the object of the present invention is a method for testing the rims of vehicle wheels, the said rims being designed to receive beaded tires, with a view to their development, characterized by the fact that it consists:

in keeping the said rim fixed, in applying, on the part of the said rim capable of receiving the beads of the said tire, rotary units of forces, of which the value of the amplitude is representative of a spectrum of the forces actually undergone by a rim when the said vehicle is to run with the latter.

Another object of the present invention is a test device for a wheel rim, capable of receiving a beaded tire, comprising means of positioning and holding the said rim, means for applying loads to the said rim, characterized by the fact that the said means for applying loads on the said rim comprise a set of controllable jacks whose heads can cooperate with the part of the rim that is to receive the bead of the tire, the said jacks being distributed all around the said rim in a substantially uniform fashion, and a control means to successively actuate the said jacks according to a predetermined cycle.

The invention will be better understood with the aid of a particular example of embodiment which will now be described, in non-limiting fashion, with reference to the attached figures in which.

Figure 1:
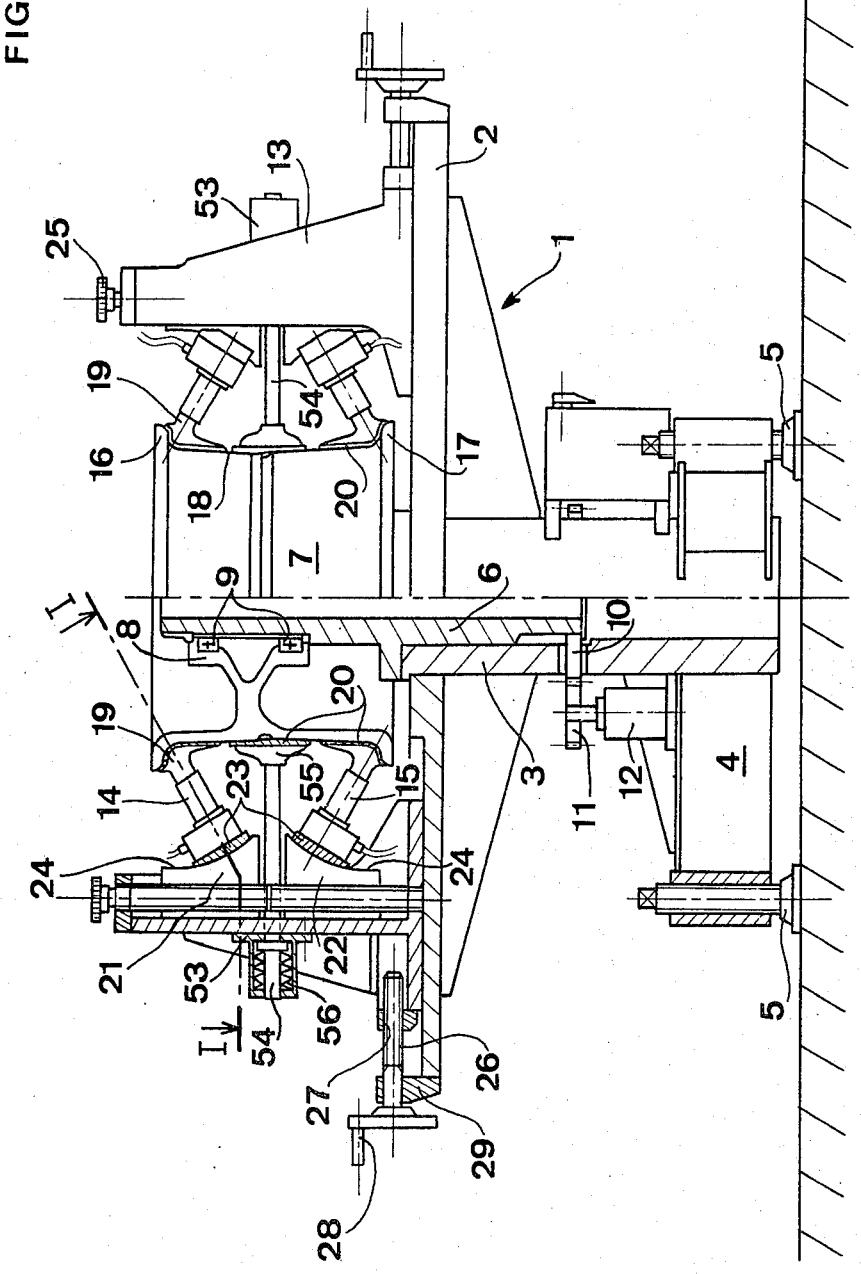
FIG. 1 represents a half-section contiguous to a half-view of the test device.

Referring to FIG. 1, the test device for vehicle wheel rims comprises a frame 1 constituted by a table 2, in the center of which there is a column 3 equipped at the base with a pedestal 4 which is supported by adjustable feet 5. Inside the column 3 there is positioned a spindle 6 bearing, at its upper extremity, a wheel 7 mounted by its hub 8 on bearings 9; the lower extremity of spindle 6 bears a first gear set 10 driven in rotation by means of a second gear set 11 mounted on an electric motor 12. This device enables the spindle to be rotated, in such a way as to conduct mechanical tests, more particularly fatigue tests on the inner rings of bearings 9, and test the flexibility of spindle 6.

Around wheel 7, supports 13 are disposed at regular angular intervals, and each one is equipped with two jacks 14 and 15, positioned one below the other, and divergently relative to supports 13, in such a way that the upper jacks 14 apply loads on the outer face, relative to hub 8, of the upper flange 16 of rim 18, and in that the lower jacks 15 apply loads on the outer face, relative to hub 8, of the lower flange 17 of this same rim 18.

By way of example, for wheels of present-day aircraft, it is possible to position some twenty supports 13 (with these two jacks), all around a wheel with a diameter of about 0.60 m.

The ends facing the wheel 7 of each of the upper and lower jacks 14 and 15, of supports 13, are equipped with a flexible shoe 19 of variable rigidity, on which a distribution pad is fixed, embodied in the form of a band of rubber 20 espousing the form of the flanges 16 and 17 of rim 18; this assembly of shoe 19 and distribution pad 20 exactly espousing the form of the beads of the tire, the use of the latter is therefore no longer necessary in this type of device.

Each support 13 is linked to these two jacks 14 and 15 by means of two skids 21 and 22, mounted slidably in support 13 and positioned one below the other; each of these skids 21 and 22 being linked to its respective jack by a rigid sole 23 adjustable in position on a concave face 24, on each skid, the skids being disposed in such a way that their concave faces 24 are back to back, in such a way as to allow an angular adjustment of jacks 14 and 15 with respect to wheel 7. Skids 21 and 22 of each support 13 are adjusted vertically or longitudinally relative to the axis of the wheel, by means of a screw 25 lodged in a tapped hole formed over the full length of the two skids, and having two reversed screw pitches so that the manipulation of screw 25 in one direction or the other, brings the skids toward or away from one another.

It is likewise possible to make a radial adjustment of each of the supports 13, relative to the axis of wheel 7; there is, in fact, a threaded rod 26 lodged in a tapped hole 27 in to supports 13, and equipped at its other extremity with a crank 28, the unthreaded part of rod 26 being held in a lateral flange 29, fixed on table 2, and serving as a journal.

There is also mounted, on each support 13, a housing 53 inside which one extremity of a shaft 54 is held, retained in translation by an external, radial shoulder. On the other extremity of each shaft 54 a shoe 55 is fixed, with variable rigidity, equipped with a rubber strip 20, applying a load on the central part of rim 18 by means of elastic elements such as discs of the "Belleville" type 56, mounted in housing 53 around shaft 54.

Figure 2:
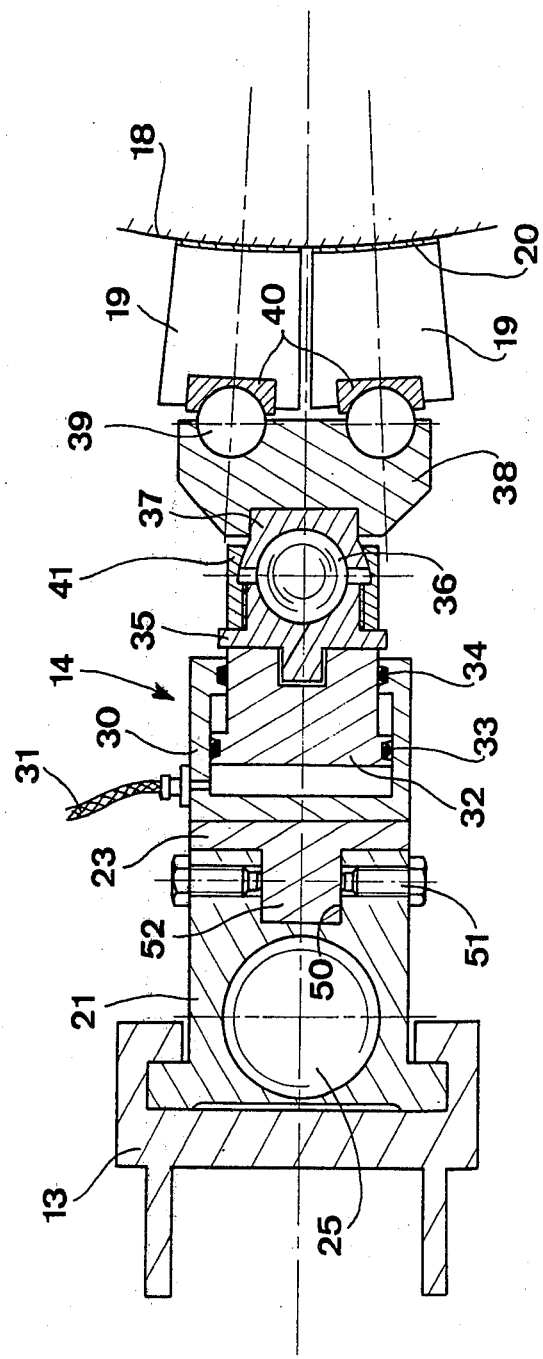
FIG. 2 represents the assembly of a jack between its support and the wheel, along section I—I of FIG. 1.

FIG. 2 shows some of the elements described above, such as support 13, having a slideway in which skids 21 and 22 (skid 21 alone being visible) can slide traversed by adjusting screw 25 insuring the back-to-back displacement of the two skids 21 and 22, which have, on their concave face, a groove 50 of constant depth, in which there is immobilized, by known means such as nippled set screws 51, whose nipple ends hold the central part 52, mounted slidably in this groove, of a sole 23 permitting the angular adjustment of the position of jack 14, whose cylinder 30 is attached to this sole 23 by means of attachment not shown.

Cylinder 30 is fed with hydraulic pressure by means of a flexible line 31; inside cylinder 30 a piston 32 is tightly mounted, equipped with gaskets 33 and 34.

When cylinder 30 is fed with pressure, the load of piston 32 is transmitted to shoes 19 by means of an endpiece 35 coupled by one of its extremities at the end of piston 32 and applying, by its opposite extremity of concave shape, a main ball 36 against a cup 37, also of concave shape, borne on one face representing a journal 38, whose opposite face applies, against shoes 19, two secondary balls 39, each one held in the latter by means of chocks 40 having a concave face to receive the balls, the end piece and the cup 37 being held firmly against the main ball 36 by means of a threaded ring 41.

Figure 3:
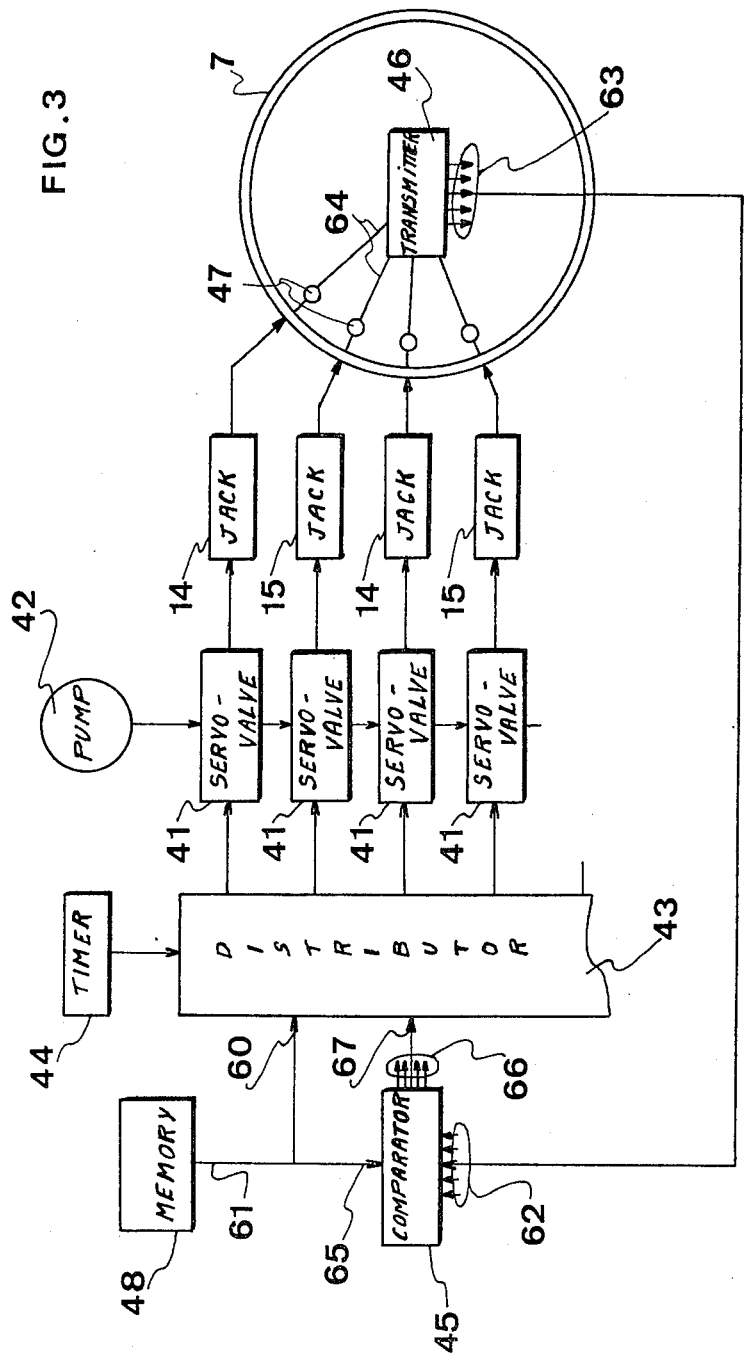
FIG. 3 represents, schematically, an installation for embodying the simulation by means of the device according to FIG. 1 and 2.

This device, as represented schematically in FIG. 3, comprises, in addition to the upper and lower jacks 14 and 15, servo-valves 41, equal in number to the jacks and controlling the latter. These servo-valves 41 are fed by a hydraulic pump 42 and are controlled by a distributor 43. The latter is synchronized by receiving electric pulses from a clock-type pulse generator 44.

The control input 60 of distributor 43 is connected to the output 61 of a memory 48 in which a set of data was introduced, of a spectrum of the stresses to which a wheel, in particular an aircraft wheel, is actually subjected, as the latter is landing and taxiing on the ground.

This device is intended more particularly for testing the wheels of aircraft in their adjustment.

The use of this device described above makes for a considerable reduction in the duration of the tests, while increasing the data on the behavior of the wheels which will then be adjusted very rapidly, and, especially, with greater safety.

Figure 4:
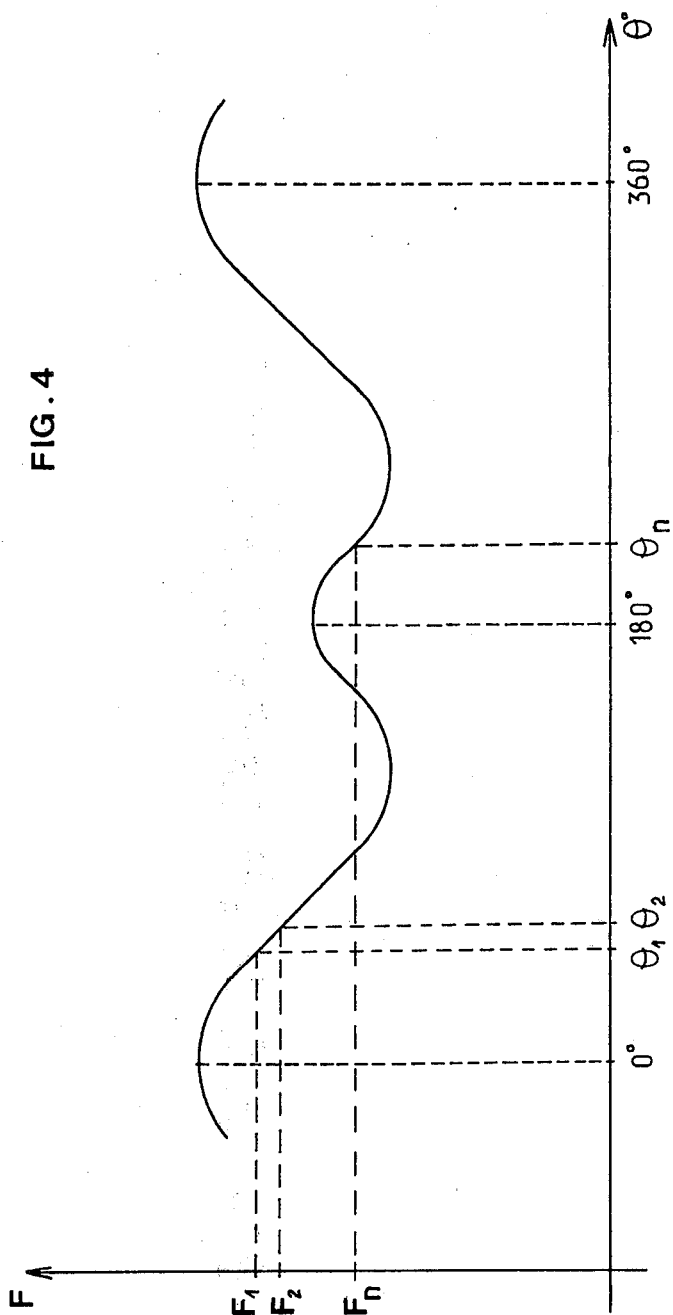
FIG. 4 represents a graph showing the stress curve on the perimeter of a wheel when it is in contact with the ground, said curve making it easy to comprehend the working of the device according to FIGS. 1 to 3.

An idea of the form of this spectrum is given in FIG. 4, representing the curve showing the values of the stresses F (in arbitrary units) all around the wheel, i.e. on its complete perimeter (over 360 deg C.).

Moreover, this device includes a comparator 45 that receives on a first set of input 62 data coming from output 63 of a transmitter 46, inputs 64, signals emitted by stress gauges 47 distributed all around wheel 7 and making it possible to determine the stresses actually applied to the wheel by the sets of jacks 14, 15.

Comparator 45 also receives, on a second set of inputs 65, the same data as those delivered to output 61 of memory 48.

And finally, output 66 of comparator 45 is linked to a second input 67 controlling distributor 43.

The test device for vehicle wheel rims described above in regard to FIGS. 1 to 4 works as follows.

The mounting of wheel 7 on spindle 6, and the positions and adjustments of the jacks having been made, hydraulic pump 42 and clocktype pulse generator 44 are started up, resulting in the feeding, respectively, of distributor 43 with electric pulses, and servo-valves 41 with hydraulic fluid under pressure. The latter are piloted by memory 48, and distributor 43, and thus transmit to jacks 14 and 15 a hydraulic control order of five cycles per second. As a result, the lower and upper flanges 16 and 17 of rim 18 will undergo stresses which will be similar to those received as the aircraft taxis over the ground, and transmitted by the beads of the tire. The plurality of jacks 14 and 15 uniformly distributed around wheel 7 are controlled in such a way that each pair of jacks 14 and 15, situated one below the other, applies a force equal to that registered by a wheel when it is running over the ground; and as a result, the stresses that wheel 7 undergoes while being in static position are equivalent to those which an identical wheel actually undergoes when in dynamic position, i.e. when running.

Thus, for example, at a moment $t_1$, a first pair of jacks 14 and 15 applies a load $F_1$ (FIG. 4) for an angular position $theta_1$ on the circumference of the wheel; a second pair of jacks 14 and 15 disposed beside the first, applies a load $F_2$ for an angular position $theta_2$, and n/th pair of jacks applies a load $F_N$ for an angular position $theta_n$.

At a moment $t_2$ closest to $t_1$, the forces $F_1, F_2 \ldots F_N$ which were applied on pairs 1, 2 . . . n of jacks respectively, are transferred to the next pair of jacks, and in so doing the forces $F_1, F_2 \ldots F_N$ are applied respectively by the pairs of jacks 2, 3 . . . n+1 and thus successively to simulate in statics a rotation of the wheel while keeping it immobile. What is obtained here, then, is the equivalent of a set of rotary forces whereof the value of their amplitude is representative of the spectrum mentioned above. Consequently, the device according to the invention reproduces, in equivalent fashion on stationary wheel 7, the loads which a wheel mounted on an aircraft receives when it is taxiing on a runway.

These gauges 47 thus record the stresses undergone by the wheel, which are then analyzed in comparator 45 in such a way as to correct, where applicable, the signals emitted by distributor 43 following the comparison between the spectrum of the stresses established in transmitter 46 and coming from wheel 7, and the true spectrum of the stresses recorded on magnetic tapes in memory 48, and previously collected on a wheel in service.

As a matter of fact, it can happen that the value of the load of a jack does not correspond to the value programmed in the memory representing the true spectrum of the stresses.

This error will then be read, then rectified, respectively by the comparator and the distributor.

This error can stem from a loss or leak in the electronic or hydraulic circuits. As a matter of fact, if, for example, a jack is not sufficiently fed, it produces a force which is less than that which should be applied on the rim. The corresponding gauge or gauges 47 will detect this deficiency and then produce a signal via transmitter 46 to notify the comparator 45 of this deficiency, at these (its) inputs 62. Since at the other inputs 65 of this comparator 45, it receives the true values of the force which should be applied, this comparator then delivers, at its output 66, an error signal (difference between the two forces) which, by means of distributor 43 will control a more substantial feed to the jack to compensate for its loss of power.

This working would then be strictly identical in the case of an excess of power, the error signal permitting a reduction in the feed to the jack so that it will exert its true power.

Naturally, when gauges 47 detect correct forces, the error signal issuing from comparator will be zero in this case, and will result in no correction of the signals coming from memory 48.

The set of data which will be collected on the gauges will be sent, for example, into a computer so that they may be analyzed and provide all sorts of information on the manner of embodying, modifying, and improving the wheel rims.

Naturally, the set of means constituting the device is known in itself, but more particularly the memory 48 will be constituted by a magnetic tape which will also be synchronized, for example, from the clock 44, or any other source of reference.

Moreover, the distributor itself will be constituted by a set, for example, of flip-flops of a number corresponding to that of the set of jacks, which will be combined with amplifiers controllable by the signals emitted by comparator 45.

I claim:

1. A device for testing a wheel having a hub and a flanged rim adapted to receive a beaded tire comprising:
    means for positioning said rim;
    means for holding said rim in place; and
    means for applying cyclic loads simulating rotation of said wheel on the part of said rim receiving the bead of said tire, the amplitude value of said loads representing the spectrum of forces actually received by a rim during use on a vehicle or aircraft.

2. The device of claim 1, wherein said means for applying cyclic loads comprise a plurality of controllable jacks positioned substantially uniformly around said rim, said jacks having heads cooperating with said part of said rim receiving said bead and further including control means for successively actuating said jacks according to a predetermined cycle.

3. The device of claim 2 further including means for checking said loads applied to said rim comprising a plurality of stress gauges acting on the perimeter of said rim and means for correcting signals generated by said control means of said jacks as a function of signals generated by said gauges.

4. The device of claim 3 wherein said means for correcting the signals comprise a transmitter receiving signals from said gauges and further including a memory containing order data and a data comparator having a comparison input receiving signals from said memory and another comparison input connected to said transmitter.

5. The device of claim 2, wherein said control means comprise an order distributor having a feed synchronizing input and a memory containing order data having an output connected to said input.

6. The device of claim 5, wherein said control means comprises clockwork means adapted to deliver pulses according to a given frequency and having an output connected to said input of said order distributor.

7. The device of claim 6, wherein said jacks include data input means, further comprising a source of high pressure fluid having an output and a servo valve having a control input connecting said output of said source with said jacks, said control input of said valve being connected to said input of said order distributor.

8. The device of claim 5, including means for checking the loads applied to said rim, said last mentioned means comprising a plurality of stress gauges acting on the perimeter of said rim and means for correcting the signals generated by said control means of said jacks as a function of signals generated by said gauges comprising a transmitter receiving signals from said gauges; and a memory containing order data and a data comparator having a comparison input receiving signals from said memory and another comparison input connected to said transmitter.

9. The device of claim 1, further including means for checking the loads applied to said rim.

10. The device of claim 9, wherein said means for applying cyclic loads comprise a plurality of controllable jacks positioned substantially uniformly around said rim; said means for checking said loads applied to said rim comprises a plurality of stress gauges acting on the perimeter of said rim and means for correcting signals generated by a control means for said jacks as a function of signals generated by said gauges.

11. A device for testing a wheel having a hub and a flanged rim adapted to receive a beaded tire comprising:
    means for positioning said rim;
    means for holding said rim in place; and
    means for applying cyclic loads stimulating rotation of said wheel on the part of said rim receiving the bead of said tire, the amplitude value of said loads representing the spectrum of forces actually received by a rim during use on a vehicle or aircraft;
    a rigid frame on which said wheel is held by its hub and a plurality of supports, said supports bearing jacks exerting loads on said rim;
    each of said supports holding two skids, each skid having a concave surface, said skids being arranged relatively one to the other such that said concave surfaces are in back-to-back relation in order to allow angular adjustment of said jacks relative to said wheel, said concave surfaces having an adjustable sole thereon;
    each of said supports bearing two jacks applying pressure on the outer face, relative to said hub, of one of two flanges of said rim;
    each jack having an end proximate to said wheel and on said end at least one flexible shoe conforming in shape with that of said outer face of said flange.

12. The device of claim 11, wherein said skids are mounted slidably on said supports.

13. The device of claim 11, wherein said frame has means for radially adjusting the position of each support relative to the axis of said wheel.

14. The device of claim 11, wherein said shoes are positioned around said wheel, are provided with distribution pads and have elastic elements for applying loads against the central part of said wheel.

15. The device of claim 14, wherein said jacks have a piston, one end of said piston being connected to an end member mounted by one of its extremities to said end of said piston and bearing with its other extremity against at least one of said shoes for transmitting thereto the load of said piston.

16. The device of claim 11, wherein a resilient pad covers the surface of said shoe facing said rim.

17. A device for testing a wheel having a hub and a flanged rim adapted to receive a beaded tire comprising:
    means for positioning said rim;

means for holding said rim in place;
and means for applying cyclic loads simulating rotation of said wheel on the part of said rim receiving the bead of said tire, the amplitude value of said loads representing the spectrum of forces actually received by a rim during use on a vehicle or aircraft;
said means for applying cyclic loads comprising a plurality of controllable jacks positioned substantially uniformly around said rim, said jacks having heads cooperating with said part of said rim receiving said bead and further including control means for successively actuating said jacks according to a predetermined cycle;
a frame, a spindle on said frame, supports for said jacks on said frame, said spindle having one end on which said hub is mounted and another connected to means for rotating same.

* * * * *